United States Patent [19]

Rambert et al.

[11] 4,115,875
[45] Sep. 26, 1978

[54] HIP PROSTHESIS

[76] Inventors: André Rambert, 27, avenue Lacassagne, Lyon, 3eme, Rhône; Gilles Bousquet, 19, avenue Béranger, Ecully, Rhone; Henri Dejour, 21, rue des Deux Fermes, Bron, Rhône, all of France

[21] Appl. No.: 788,827

[22] Filed: Apr. 19, 1977

[30] Foreign Application Priority Data

Apr. 26, 1976 [FR] France .................................. 76 13189

[51] Int. Cl.² .............................................. A61F 1/24
[52] U.S. Cl. ................................. 3/1.913; 128/92 CA
[58] Field of Search .................................. 3/1.9–1.913; 128/92 CA, 92 C

[56] References Cited

U.S. PATENT DOCUMENTS

| 2,719,522 | 10/1955 | Hudack | 128/92 CA |
|---|---|---|---|
| 3,806,957 | 4/1974 | Shersher | 3/1.913 |
| 3,815,157 | 6/1974 | Skorecki et al. | 3/1.91 |
| 3,894,297 | 7/1975 | Mittelmeier et al. | 3/1.912 |
| 4,001,897 | 1/1977 | Rambert et al. | 3/1.913 |

FOREIGN PATENT DOCUMENTS 1,017,927  10/1952  France .................................. 128/92 CA

OTHER PUBLICATIONS

Journal of Bone & Joint Surgery, vol. 46–A, No. 7, Oct. 1964, Advertisement p. 54, Wright Mfg. Co.

Primary Examiner—Ronald L. Frinks
Attorney, Agent, or Firm—Browdy and Neimark

[57] ABSTRACT

The male and female parts of a hip prosthesis each comprise two parts, a base fixed to the bone, and an active organ attached removably to the base. The upper face of the base has a truncated conical bore with a threaded bore at the bottom. The active member has a conically shaped projection with a threaded end which matches the bore in the base and which is screwed in the base to effectively lock the active member to the base. Diametrically opposite flat parts on the base and active member are provided to allow the active member to rotate while preventing the base from rotating.

2 Claims, 2 Drawing Figures

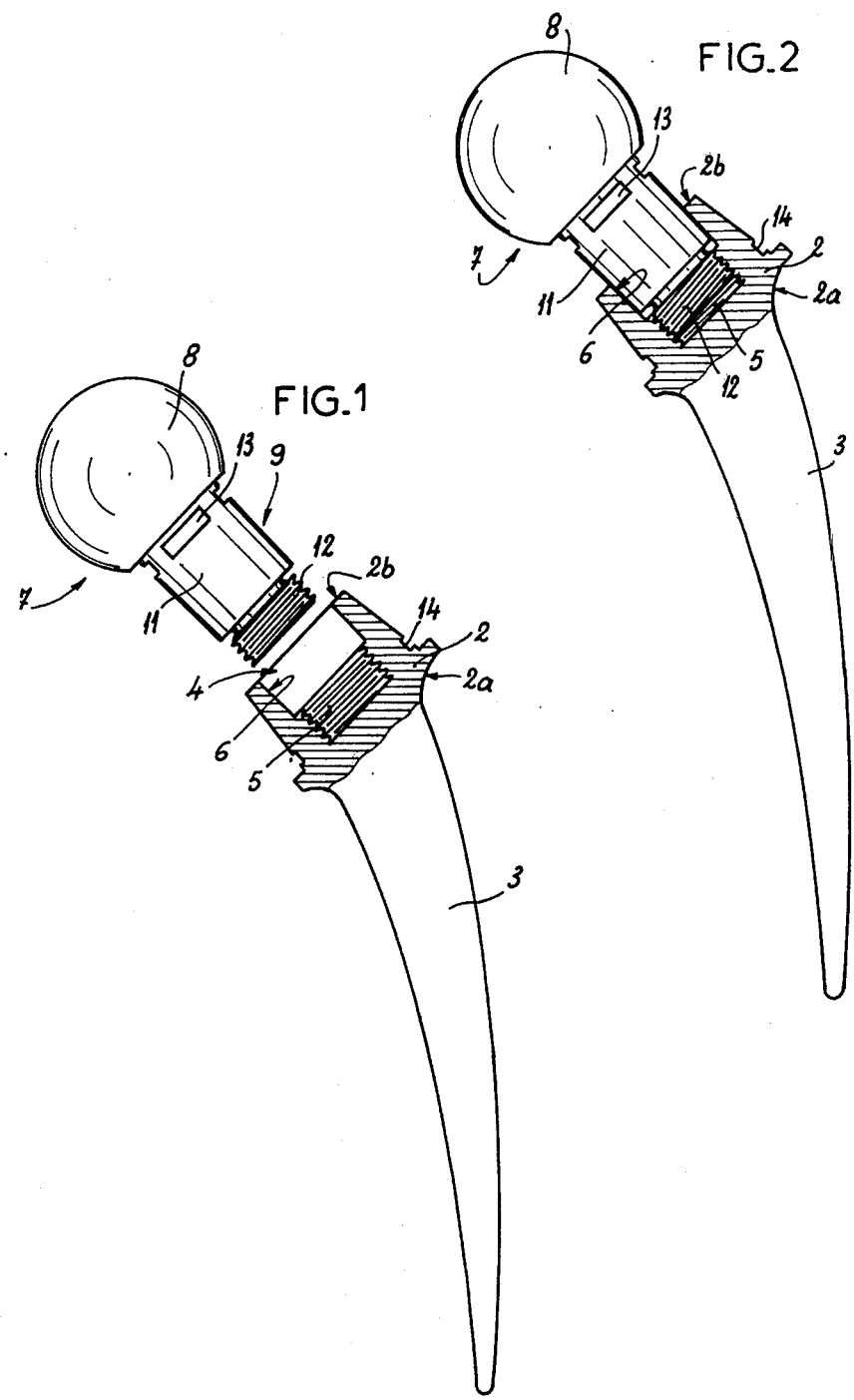

HIP PROSTHESIS

FIELD OF THE INVENTION

The present invention relates to a hip prosthesis, and more particularly to an improved ball and socket type hip prosthesis with the elements made of two parts, a base fixed to the bone and an active organ attached removably to the base.

BACKGROUND OF THE INVENTION

The prosthesis is of the type, as described for example in applicant's U.S. Pat. No. 4,001,897, with two parts forming a ball-and-socket joint. One part, female, is designed to replace the hip socket and the other, male, is designed to replace the head of the femur. Each of the two elements of this type of prosthesis is composed of two parts, a base attached irremovably to the bone and an active organ attached removably to the base. The active organ is composed of either a male or female sphere.

According to a particular embodiment of the prosthesis, as described in applicant's U.S. Pat. No. 4,001,897, the base of the male element is a plate designed to bear on the upper end of the femur, the bearing face of which has a rod designed to engage the femur, and on the other face of which is mounted a split collar equipped with a tightening bolt and having a threaded bore and a smooth bore. The active organ of this male element is composed of a sphere provided with a cylindrical radial projection having a threaded zone designed to engage the threaded bore of the split collar of the base and a smooth part designed to tighten it in the collar.

Attachment of the active organ to the base of this male element is thus provided by screwing the threaded part of the radial projection of the active element into the threaded bore of the base and by tightening of the split collar by means of a tightening bolt which ensures that the two elements are rotationally immovable with respect to each other.

It will readily be understood that for effective locking it is necessary for the collar to exert a powerful tightening force on the smooth part of the radial projection of the active element. To obtain this powerful tightening force, it is necessary to have a bolt able to withstand very large twisting and pulling stresses without risk of breaking, so that bolts with a large cross section are used. As a result, the collar must be oversized to accommodate the tightening bolt, leading to relatively large male element bases.

SUMMARY OF THE INVENTION

It is an object of the present invention to overcome this disadvantage of an oversize collar to accommodate a tightening bolt of large cross section.

For this purpose, the present invention relates to a hip prosthesis, especially of the type with a male element base composed of a plate designed to bear on the upper sectioned end of the femur whose bearing face has a rod designed to engage the femur and, an active element formed by a sphere provided with a radial projection with a smooth zone followed by a threaded terminal zone.

In this prosthesis the smooth part of the radial projection of the active organ has a conical profile with a slight taper in the direction of its free end. The face opposite the face of the base has a threaded bore able to receive the threaded end of the radial projection of the active organ. Above this threaded bore is a conical bearing surface whose profile matches the smooth part of the radial projection of the active organ. Means for allowing the active organ to rotate and preventing the base from rotating are provided to facilitate mounting of the active organ on its base and removal of the active organ.

Thus an assembly of two matching cones with a slight taper and very effective locking of the active organ in its base is obtained, with no danger of any organ breaking.

Advantageously, the means for allowing the active organ to rotate and preventing its base from rotating are each composed of at least two diametrically opposite flat parts.

Locking or unlocking of the active organ relative to its base can thus be easily accomplished with the aid of two keys.

BRIEF DESCRIPTION OF THE DRAWINGS

The invention will be better understood with the aid of the description hereinbelow referring to the attached drawings which represent an embodiment of the male element of this prosthesis as a nonlimitative example, in which:

FIG. 1 is a side elevation of the male element before assembly;

FIG. 2 is a view of the male element similar to FIG. 1 after assembly.

DESCRIPTION OF THE PREFERRED EMBODIMENT

The male hip prosthesis element has a base 2 whose lower face 2a, designed to bear on the upper sectioned end of the femur, has a rod 3 designed to engage and be sealed into the cavum medullare of the femur. The opposite face 2b of the base 2 has a cavity 4 composed of a threaded bore 5 at the bottom and a truncated conical bore 6 situated above the threaded bore 5 with a slight taper toward threaded bore 5.

Active organ 7 of the male prosthesis element, which is designed to be accommodated in the socket of the patient's hip, is composed essentially of a sphere 8 provided with a radial projection 9 having a smooth truncated conical part 11 matching truncated conical bore 6 of cavity 4 and a threaded terminal part 12 screwable into threaded bore 5 of base 2.

It will readily be understood that after screwing threaded part 12 of radial projection 9 or active organ 7 into threaded bore 5, male cone 11 of active organ 7 is locked into female conical bore 6 of base 2. This locking can be extremely effective with no danger of threaded parts 5 and 12 breaking.

In the embodiment illustrated in FIGS. 1 and 2, to permit active organ 7 to rotate and to prevent base 2 from rotating, flat parts 13 and 14 diametrically opposite pairwise have been provided, into which a key can easily be engaged.

Flat parts 14 provided on base 2 are necessary so that there be no risk of damaging the seal of the base 2 in the patient's femur upon repeated operation of assembling and removing active organ 7.

The invention is not confined to the embodiment of the prosthesis described hereinabove as a nonlimitative example; on the contrary, it embraces all other embodiments within the scope of the invention.

What is claimed is:

1. Prosthesis of the male-female ball-and-socket type comprising:
    a base of the male element composed of a plate designed to bear on the upper sectioned end of the femur, the bearing face of said plate having a rod designed to engage the femur end,
    an active organ comprising a sphere provided with a radial projection having a smooth part followed by a terminal threaded zone, said smooth part of said radial projection of said active organ having a conical shape with a slight taper toward the free end thereof, the face opposite said bearing face of the base having a threaded bore able to receive the threaded end of said radial projection of said active organ, and a conical bearing surface above said threaded bore with a shape matching said smooth part of said radial projection of said active organ, and
    means for allowing said active organ to rotate and preventing said base from rotating, said means being provided to facilitate assembly of said active organ on said base and removing said active organ.

2. Prosthesis according to claim 1, wherein said means for rotating said active organ and preventing said base from rotating comprises at least two diametrically opposite flat parts.